US008286977B2

(12) United States Patent
Butler et al.

(10) Patent No.: US 8,286,977 B2
(45) Date of Patent: Oct. 16, 2012

(54) MEDICAL CART

(75) Inventors: Christiano Butler, Bardonia, NY (US); Steven Wicksman, Putnam Valley, NY (US); Kazuna Tanaka, Cos Cob, CT (US); Jeffrey S. Kapec, Westport, CT (US); Yukiko Naoi, New York, NY (US)

(73) Assignee: MELA Sciences, Inc., Irvington, NY (US)

( * ) Notice: Subject to any disclaimer, the term of this patent is extended or adjusted under 35 U.S.C. 154(b) by 452 days.

(21) Appl. No.: 12/512,775

(22) Filed: Jul. 30, 2009

(65) Prior Publication Data
US 2011/0025007 A1  Feb. 3, 2011

(51) Int. Cl.
B62B 3/00 (2006.01)

(52) U.S. Cl. .................. 280/47.35; 280/47.34

(58) Field of Classification Search ............ 280/35, 280/47.34, 47.35, 79.11, 79.2, 79.3; 248/616, 248/125.8, 188.5, 333, 346.06, 551–553, 248/183.2, 176.1, 161; 361/679.41
See application file for complete search history.

(56) References Cited

U.S. PATENT DOCUMENTS

| | | | |
|---|---|---|---|
| 4,841,134 A | | 6/1989 | Hida et al. |
| D338,272 S * | | 8/1993 | Cunagin et al. ............. D24/167 |
| 5,314,243 A * | | 5/1994 | McDonald et al. .......... 312/215 |
| 5,348,324 A * | | 9/1994 | Trotta ............................ 280/35 |
| D352,106 S * | | 11/1994 | Fanney et al. ................ D24/185 |
| 5,536,084 A * | | 7/1996 | Curtis et al. .................. 700/240 |
| 5,564,803 A * | | 10/1996 | McDonald et al. .......... 312/215 |
| 5,623,869 A * | | 4/1997 | Moss et al. ...................... 108/43 |
| 5,702,115 A * | | 12/1997 | Pool ............................ 280/47.35 |
| D389,917 S * | | 1/1998 | Hornback et al. ........... D24/186 |
| 5,765,842 A * | | 6/1998 | Phaneuf et al. ............. 280/47.35 |
| 5,806,943 A * | | 9/1998 | Dell et al. .................... 312/223.3 |
| D406,894 S * | | 3/1999 | Menhennett et al. ........ D24/169 |
| D412,748 S * | | 8/1999 | Nabarro ....................... D24/186 |
| 6,022,088 A * | | 2/2000 | Metzler ......................... 312/209 |
| 6,081,612 A | | 6/2000 | Gutkowicz-Krusin et al. |
| D430,867 S * | | 9/2000 | Smith et al. .................. D14/308 |
| D434,502 S * | | 11/2000 | Gallant ........................ D24/185 |
| 6,189,843 B1 * | | 2/2001 | Pfister .......................... 248/161 |
| 6,208,749 B1 | | 3/2001 | Gutkowicz-Krusin et al. |
| D446,861 S * | | 8/2001 | Meziere et al. .............. D24/169 |
| 6,307,957 B1 | | 10/2001 | Gutkowicz-Krusin et al. |
| 6,339,732 B1 * | | 1/2002 | Phoon et al. ................. 700/237 |
| 6,374,752 B1 * | | 4/2002 | Walser ....................... 108/50.01 |

(Continued)

FOREIGN PATENT DOCUMENTS

JP       2007-293663      11/2007

(Continued)

OTHER PUBLICATIONS

Slides depicting a mock user interface of a prototype medical cart, American Academy of Dermatology conference (Feb. 2009), 19 pages.

(Continued)

*Primary Examiner* — John R Olszewski
*Assistant Examiner* — Jacob Meyer
(74) *Attorney, Agent, or Firm* — Fish & Richardson P.C.

(57) ABSTRACT

Among other things, a movable medical device cart has a work surface on a pedestal and legs under the pedestal, an electronic device accessible at the work surface in connection with performing a medical procedure, and a computer mounted near a bottom of the pedestal to sink heat away from the computer.

20 Claims, 12 Drawing Sheets

U.S. PATENT DOCUMENTS

Figure 1:
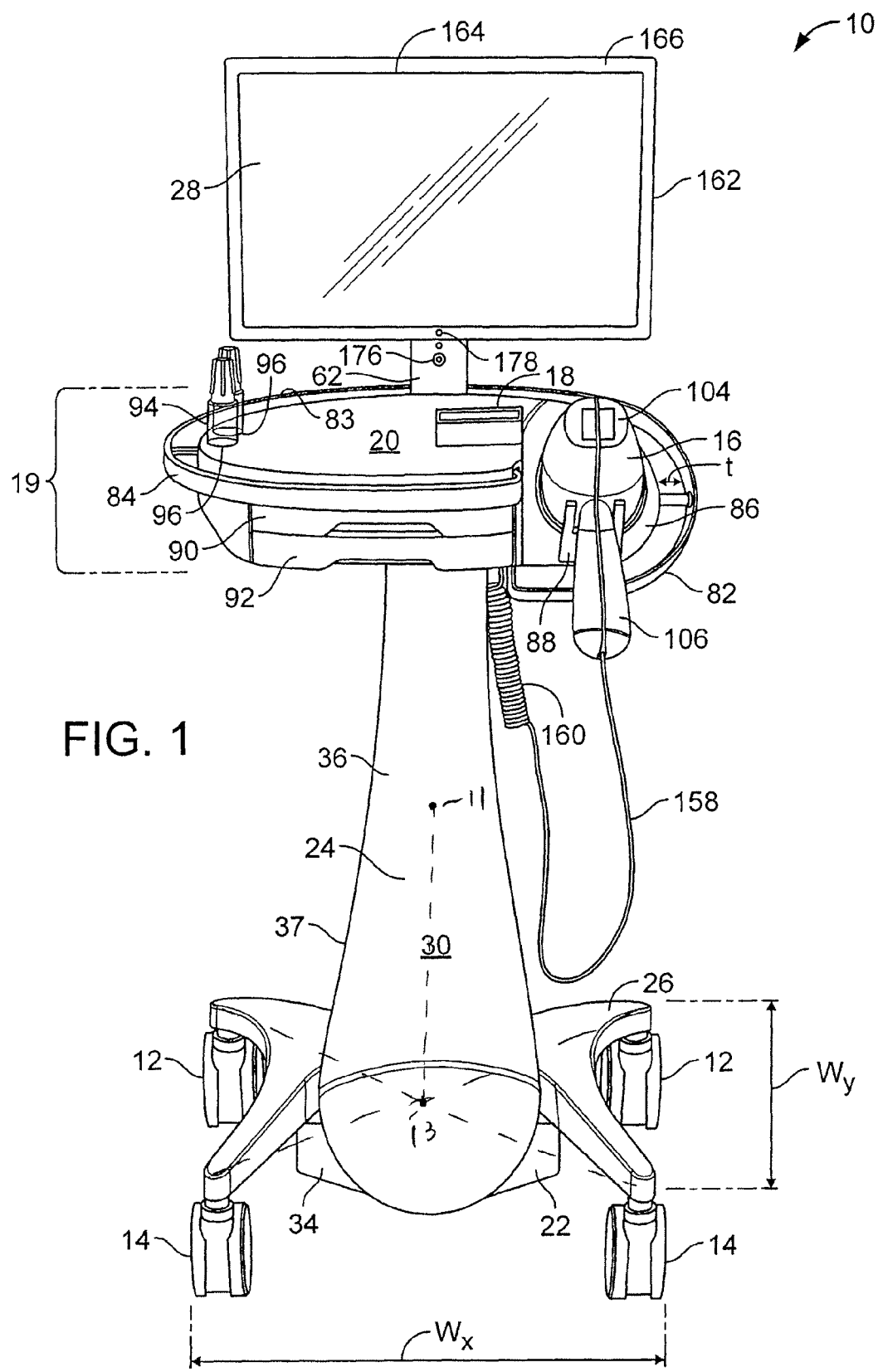

| | | | |
|---|---|---|---|
| 6,378,816 B1* | 4/2002 | Pfister | 248/161 |
| 6,435,109 B1* | 8/2002 | Dell et al. | 108/144.11 |
| 6,457,647 B1 | 10/2002 | Kurihashi et al. | |
| D467,001 S * | 12/2002 | Buczek et al. | D24/172 |
| 6,493,217 B1* | 12/2002 | Jenkins, Jr. | 361/679.6 |
| 6,493,220 B1* | 12/2002 | Clark et al. | 361/679.41 |
| 6,563,616 B1 | 5/2003 | Brenner | |
| 6,626,445 B2* | 9/2003 | Murphy et al. | 280/47.34 |
| 6,626,558 B2 | 9/2003 | Momot et al. | |
| 6,654,378 B1* | 11/2003 | Mahany et al. | 370/401 |
| 6,655,545 B1* | 12/2003 | Sonneborn | 221/7 |
| 6,657,798 B1 | 12/2003 | Kabelevs et al. | |
| D486,915 S * | 2/2004 | Warschewske et al. | D24/185 |
| 6,688,634 B2* | 2/2004 | Noffsinger | 280/651 |
| 6,710,947 B1 | 3/2004 | Momot et al. | |
| 6,715,722 B2* | 4/2004 | Roberts | 248/129 |
| 6,722,673 B1* | 4/2004 | Hamlin | 280/47.35 |
| 6,942,417 B2* | 9/2005 | Schwarzbich | 403/109.1 |
| D512,508 S * | 12/2005 | Mesaros | D24/185 |
| 6,980,419 B2* | 12/2005 | Smith et al. | 361/679.41 |
| D517,768 S * | 3/2006 | Arceta | D34/14 |
| D518,267 S * | 3/2006 | Arceta | D34/14 |
| 7,009,840 B2* | 3/2006 | Clark et al. | 361/679.41 |
| 7,102,672 B1 | 9/2006 | Jacobs | |
| 7,127,094 B1 | 10/2006 | Elbaum et al. | |
| 7,130,190 B1* | 10/2006 | Baker | 361/695 |
| D531,728 S * | 11/2006 | Helgeson | D24/164 |
| 7,191,950 B1* | 3/2007 | Petrovich et al. | 235/472.02 |
| D539,794 S * | 4/2007 | Rossini et al. | D14/302 |
| D544,962 S * | 6/2007 | Diener et al. | D24/186 |
| D548,918 S * | 8/2007 | Nussberger et al. | D34/17 |
| D550,362 S * | 9/2007 | Olivera et al. | D24/185 |
| D552,740 S * | 10/2007 | Park | D24/186 |
| 7,278,583 B2 | 10/2007 | Lee | |
| 7,311,254 B2* | 12/2007 | Olsen | 235/440 |
| D561,342 S * | 2/2008 | Zimmer | D24/185 |
| 7,338,055 B2* | 3/2008 | Fuentes | 280/79.3 |
| 7,341,198 B2 | 3/2008 | Nishizawa et al. | |
| 7,352,570 B2* | 4/2008 | Smith et al. | 361/679.41 |
| D568,258 S * | 5/2008 | Adam | D13/163 |
| D568,481 S * | 5/2008 | Martinson | D24/185 |
| 7,367,571 B1* | 5/2008 | Nichols | 280/47.18 |
| 7,401,796 B1* | 7/2008 | Greco | 280/47.35 |
| 7,461,825 B2* | 12/2008 | Olivera et al. | 248/282.1 |
| D585,991 S * | 2/2009 | Helgeson et al. | D24/185 |
| 7,490,837 B2* | 2/2009 | Pond et al. | 280/47.35 |
| D588,272 S | 3/2009 | Meiser | |
| D596,420 S * | 7/2009 | Yoshida | D6/396 |
| 7,562,883 B2* | 7/2009 | Livengood et al. | 280/87.01 |
| 7,564,359 B2 | 7/2009 | Koh et al. | |
| 7,591,786 B2* | 9/2009 | Holmberg et al. | 600/437 |
| 7,594,668 B2* | 9/2009 | Arceta et al. | 280/47.35 |
| 7,612,999 B2* | 11/2009 | Clark et al. | 361/679.4 |
| 7,621,544 B2* | 11/2009 | Rossini | 280/79.3 |
| 7,654,261 B1* | 2/2010 | Rockhold | 128/204.18 |
| D613,866 S * | 4/2010 | Tanaka et al. | D24/185 |
| D613,867 S * | 4/2010 | Tanaka et al. | D24/185 |
| 7,719,420 B2* | 5/2010 | Christie et al. | 340/542 |
| 7,791,866 B2* | 9/2010 | Clark et al. | 361/679.01 |
| 7,806,376 B2* | 10/2010 | Song et al. | 248/177.1 |
| D629,523 S * | 12/2010 | Porter et al. | D24/185 |
| 7,849,859 B2* | 12/2010 | Bochner et al. | 128/845 |
| 7,859,836 B2* | 12/2010 | Bae | 361/679.55 |
| 7,884,735 B2* | 2/2011 | Newkirk | 340/691.6 |
| D639,960 S * | 6/2011 | Boudier et al. | D24/185 |
| D643,535 S * | 8/2011 | Ross et al. | D24/164 |
| 7,990,691 B2* | 8/2011 | Clark et al. | 361/679.01 |
| 8,056,910 B2* | 11/2011 | Deavila | 280/47.35 |
| 8,075,071 B1* | 12/2011 | Whittall | 312/249.12 |
| D652,521 S * | 1/2012 | Ross et al. | D24/185 |
| 8,109,527 B2* | 2/2012 | Bustle et al. | 280/47.35 |
| D657,470 S * | 4/2012 | Schon et al. | D24/186 |
| 2001/0035702 A1* | 11/2001 | Murphy et al. | 312/229 |
| 2002/0004863 A1 | 1/2002 | Kazo | |
| 2002/0013640 A1* | 1/2002 | Phoon et al. | 700/237 |
| 2002/0040954 A1* | 4/2002 | Roberts | 248/121 |
| 2002/0076954 A1 | 6/2002 | Chen et al. | |
| 2003/0155731 A1* | 8/2003 | Ditges et al. | 280/47.35 |
| 2003/0201697 A1* | 10/2003 | Richardson | 312/209 |
| 2003/0222548 A1* | 12/2003 | Richardson et al. | 312/209 |
| 2004/0165348 A1* | 8/2004 | Clark et al. | 361/686 |
| 2004/0179332 A1* | 9/2004 | Smith et al. | 361/681 |
| 2004/0217564 A1* | 11/2004 | Ditges et al. | 280/79.3 |
| 2004/0262867 A1* | 12/2004 | Arceta et al. | 280/47.35 |
| 2005/0017468 A1* | 1/2005 | Gallant et al. | 280/47.35 |
| 2005/0035198 A1* | 2/2005 | Wilensky | 235/383 |
| 2005/0200707 A1 | 9/2005 | Yogesan et al. | |
| 2006/0015752 A1 | 1/2006 | Krueger | |
| 2006/0094277 A1 | 5/2006 | Yang et al. | |
| 2006/0125356 A1* | 6/2006 | Meek et al. | 312/215 |
| 2006/0130714 A1* | 6/2006 | Jones et al. | 108/106 |
| 2006/0186209 A1 | 8/2006 | Narendra et al. | |
| 2006/0255553 A1* | 11/2006 | Gust et al. | 280/47.34 |
| 2006/0278723 A1 | 12/2006 | Dan et al. | |
| 2007/0001413 A1* | 1/2007 | Rossini | 280/47.35 |
| 2007/0185390 A1* | 8/2007 | Perkins et al. | 600/300 |
| 2007/0216267 A1* | 9/2007 | Johanning | 312/294 |
| 2007/0228680 A1* | 10/2007 | Reppert et al. | 280/47.35 |
| 2008/0031537 A1 | 2/2008 | Gutkowicz-Krusin et al. | |
| 2008/0078071 A1* | 4/2008 | Gong | 24/373 |
| 2008/0214907 A1 | 9/2008 | Gutkowicz-Krusin et al. | |
| 2008/0251661 A1* | 10/2008 | Rossini | 248/176.1 |
| 2008/0252045 A1* | 10/2008 | Rossini et al. | 280/659 |
| 2008/0255448 A1* | 10/2008 | Zhu et al. | 600/437 |
| 2008/0312952 A1 | 12/2008 | Gulfo et al. | |
| 2009/0015116 A1* | 1/2009 | Arceta et al. | 312/209 |
| 2009/0060304 A1 | 3/2009 | Gulfo et al. | |
| 2009/0101219 A1* | 4/2009 | Martini et al. | 137/565.29 |
| 2009/0154781 A1 | 6/2009 | Bogdan | |
| 2009/0212518 A1* | 8/2009 | Bustle et al. | 280/47.35 |
| 2009/0212670 A1* | 8/2009 | Bustle et al. | 312/209 |
| 2009/0261549 A1* | 10/2009 | Kral | 280/47.35 |
| 2009/0315287 A1* | 12/2009 | Rossini | 280/47.35 |
| 2009/0319079 A1* | 12/2009 | Arceta et al. | 700/228 |
| 2010/0148458 A1* | 6/2010 | Ross et al. | 280/47.34 |
| 2010/0213679 A1* | 8/2010 | Smith et al. | 280/47.35 |
| 2011/0024507 A1 | 2/2011 | Tanaka et al. | |
| 2011/0042911 A1* | 2/2011 | Kozlowski, Jr. et al. | 280/47.35 |
| 2011/0272902 A1* | 11/2011 | Arceta et al. | 280/47.35 |
| 2012/0118981 A1 | 5/2012 | Tanaka et al. | |
| 2012/0126503 A1 | 5/2012 | Butler et al. | |

FOREIGN PATENT DOCUMENTS

| | | |
|---|---|---|
| WO | WO 2005/072638 | 8/2005 |
| WO | WO 2007/038262 | 4/2007 |
| WO | WO 2011/014614 | 2/2011 |
| WO | WO 2011/014656 | 2/2011 |

OTHER PUBLICATIONS

Script used during demonstration of a mock user interface of a prototype medical cart, American Academy of Dermatology conference (Feb. 2009), 5 pages.

Photographs of a medical cart used in clinical trials (Dec. 2006-Jul. 2008), 11 pages.

Electro-Optical Sciences, Inc., Needham & Co. 7th Annual Bio/MedTech Conferene, Presentation re MELAFIND (Jun. 11, 2008, 35 pages).

Electro-Optical Sciences, Inc. 2008 Annual Report (Apr. 15, 2009, 88 pages).

Electro-Optical Sciences, Inc. 2007 Annual Report (Apr. 15, 2008, 96 pages).

Van Dusen, A., "Invasive biopsies may soon be a thing of the past if these detection methods prove effective," *Forbes* (Aug. 22, 2008, 3 pages).

Thumbnail image titled "eos-moneyshot.jpg" downloaded from http://images.google.com on Jul. 27, 2009, and source code indicating that the thumbnail image was originally available on http://www.daniellicalzi.com on Jun. 2009, 2 pages.

Howard Teacher's Pet—Revolutionary Classroom Management, http://www.howardcomputers.com/petcart/, downloaded from internet on Jul. 30, 2009, 6 pages.

FreelanceDesigners.org, Daniel LiCalzi, Live Beta, downloaded from the internet on Jun. 26, 2009, 3 pages.

Tanaka Kapec Design Group, Inc., Strategic Product Development + Industrial Design, http://www.tkdg.com/, downloaded from the internet on Jun. 26, 2009, 3 pages.
U.S. Appl. No. 11/761,816.
International Search Report and Written Opinion for App. Ser. No. PCT/US2010/043713, dated Apr. 20, 2011, 7 pages.
International Search Report and Written Opinion for App. Ser. No. PCT/US2010/043644, dated Apr. 29, 2011, 9 pages.
International Preliminary Report on Patentability for App. Ser. No. PCT/US2010/043644, dated Jan. 31, 2012, 6 pages.
International Preliminary Report on Patentability for App. Ser. No. PCT/US2010/043713, dated Jan. 31, 2012, 6 pages.
U.S. Appl. No. 29/341,111.
U.S. Appl. No. 29/341,114.
U.S. Appl. No. 12/512,895.
U.S. Appl. No. 13/387,652.
U.S. Appl. No. 13/360,447.

* cited by examiner

MEDICAL CART

TECHNICAL FIELD

This description relates to a medical cart.

BACKGROUND

A medical cart sometimes has wheels to enable it to be moved easily from one room to another or moved within a room, so that a procedure can be performed or another use made of the medical cart. Typical medical carts also hold equipment, such as electronic equipment, that relates to the procedure or other use.

SUMMARY

In general, in an aspect, a movable medical device cart has a work surface on a pedestal and legs under the pedestal, an electronic device accessible at the work surface in connection with performing a medical procedure, and a computer mounted near a bottom of the pedestal to sink heat away from the computer.

Implementations may include one or more of the following features. The legs comprise a metal. The computer is mounted within the pedestal. There are connections from the computer to the electronic device inside the pedestal. The electronic device comprises a display. The electronic device comprises a receptacle for a memory card. The electronic device comprises a probe for imaging skin of a patient. The work surface is at a height for an adult to work, and the breadth of the work surface is less than one-half of a height of the pedestal. The work surface is at a height for an adult to work, and the breadth of the legs less than one-half of the height of the work surface. There are four legs. Each of the legs rides on a caster. The movable medical cart is stable on a surface having a tilt angle up to about 15 degrees. The apparatus also includes a handle for a user to hold and move the movable medical device. The handle is in an ergonomic shape. The handle includes a metal core and a plastic shell. The pedestal is hollow and houses wires for power supplies to the electronic device. There are one or more USB ports adjacent to the work surface. The electronic device comprises a touch monitor. The monitor is set in a bezel of a casing. The casing is assembled about the monitor by snapping. Two of the legs span a width of about 18 inches to about 20 inches along a first direction. Two of the legs span a width of about 15 inches to about 18 inches along a second direction different from the first direction. A center of the gravity of the apparatus including the medical cart, the electronic device, and the computer is about ⅓ of a total height of the apparatus from a floor on which the medical device stands.

In general, in another aspect, a movable medical device cart has a work surface on a pedestal and legs between the pedestal and a floor, and a handle that extends along at least half of a perimeter of the work surface. The handle is attached to the work surface by spars at attachment locations along a length of the handle. The handle is spaced from the work surface by a gap that is large enough to receive a hand of a user that is holding the handle. The handle has a cross-section that enables a user's hand to grasp the handle at locations along its length. The handle has an elongated steel core. The handle has a non-metal molded sheathing on the core.

These and other features and aspects, and combinations of them, can be expressed as methods, apparatus, systems, program products, as means for performing a function, and in other ways.

Other advantages and features will become apparent from the description and the claims.

DESCRIPTION

Figure 2:
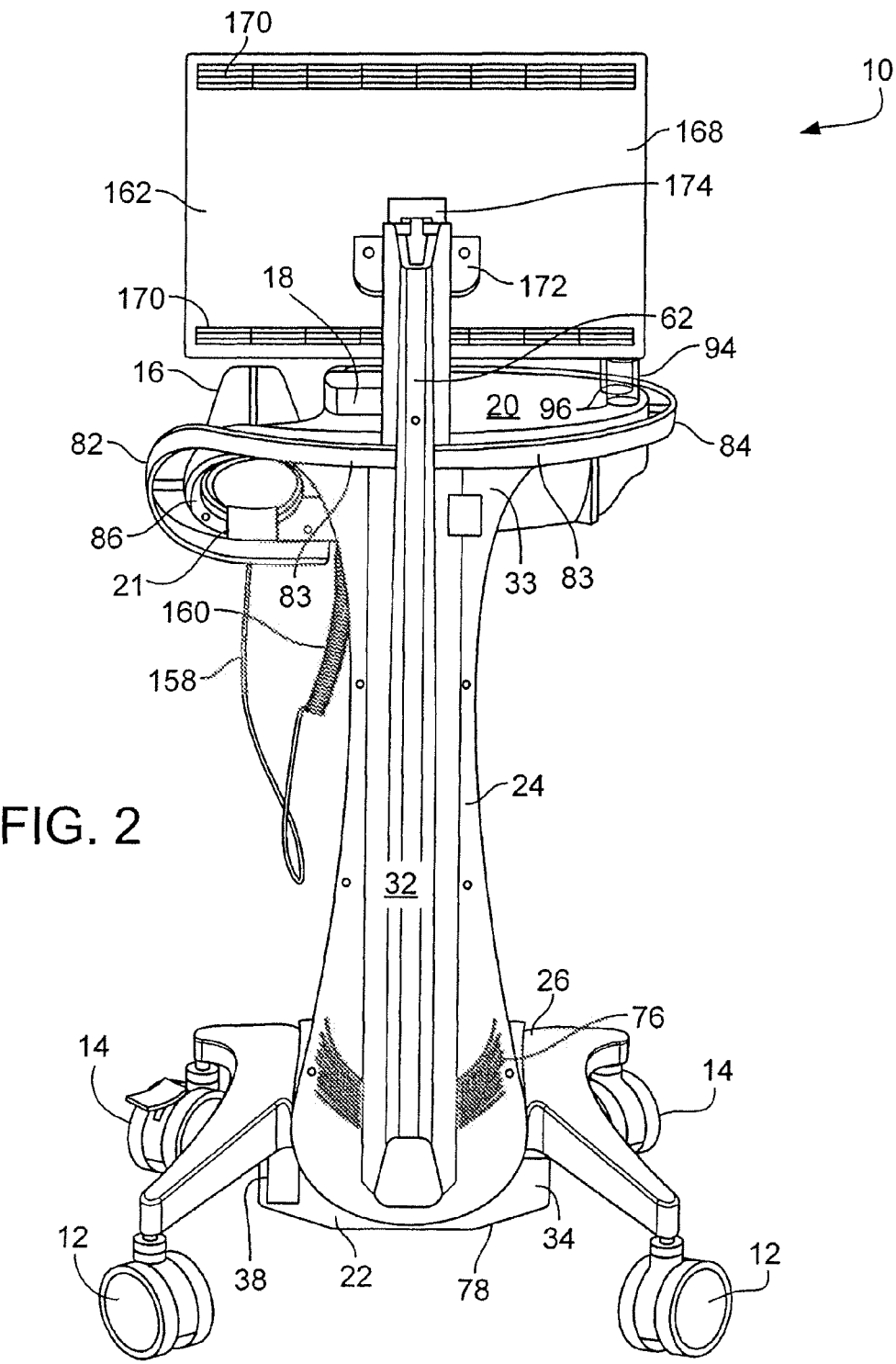
Figure 3:
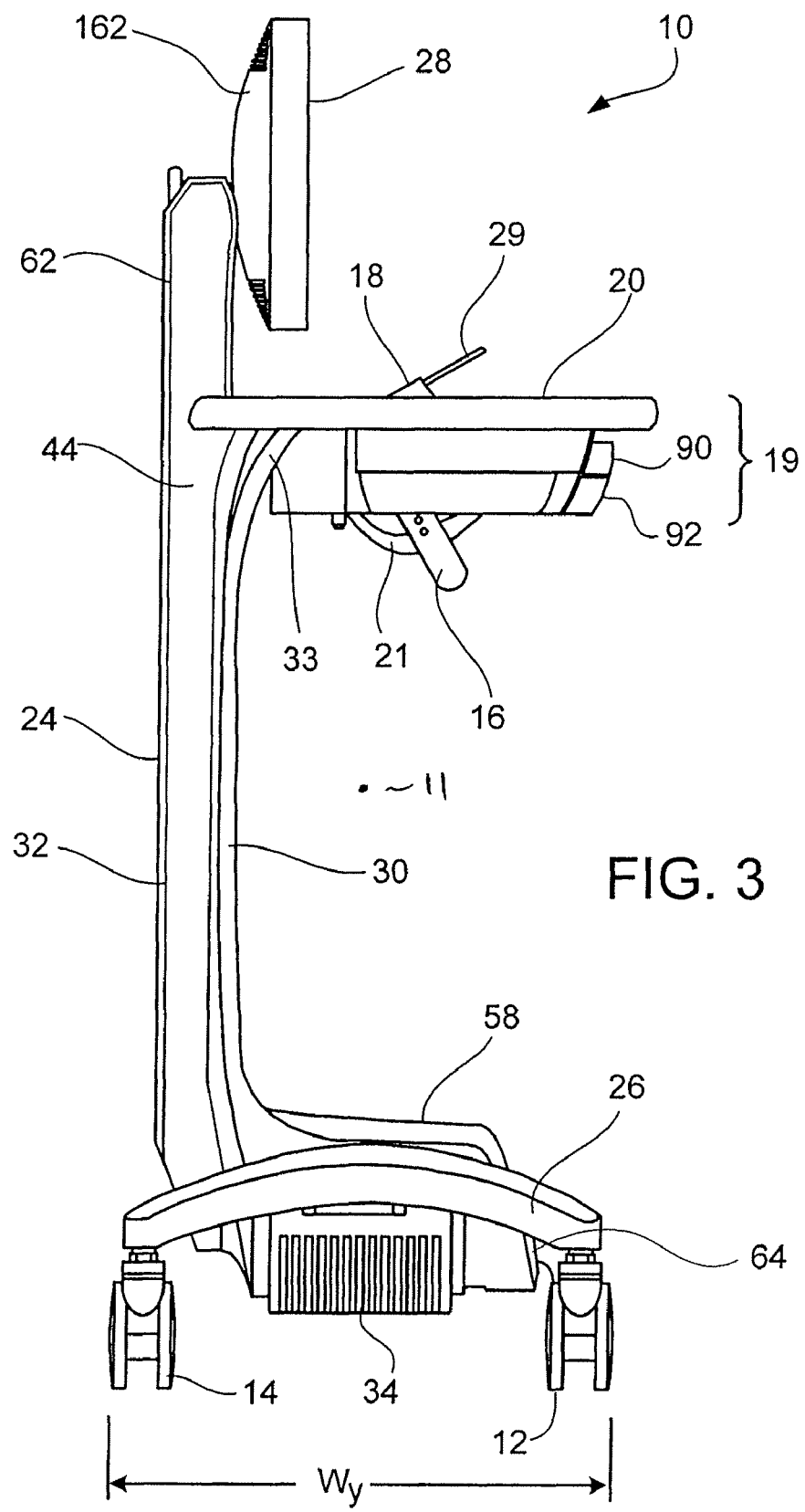
Figure 3A:
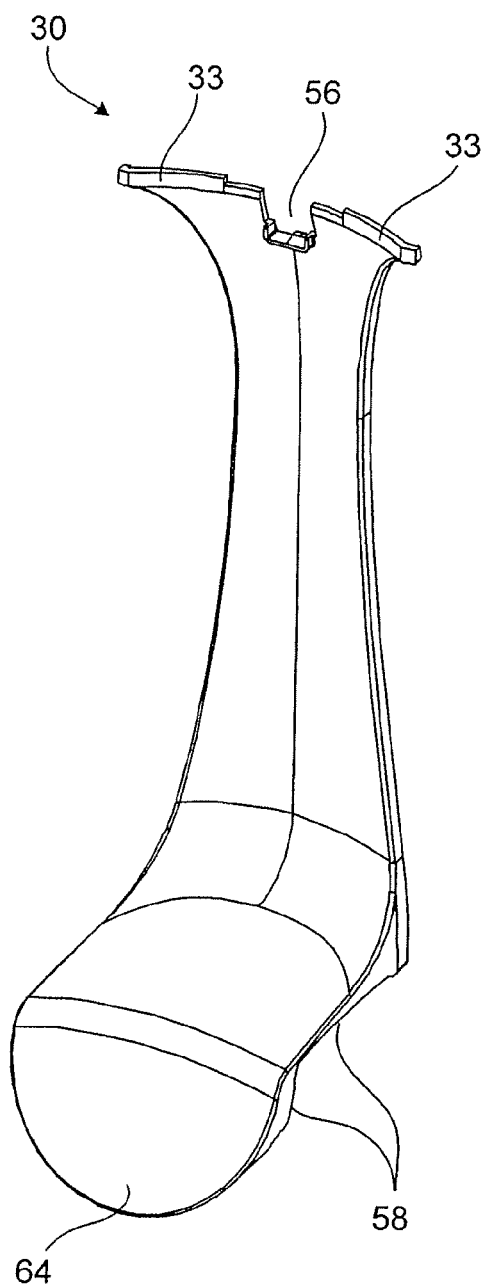
Figure 3B:
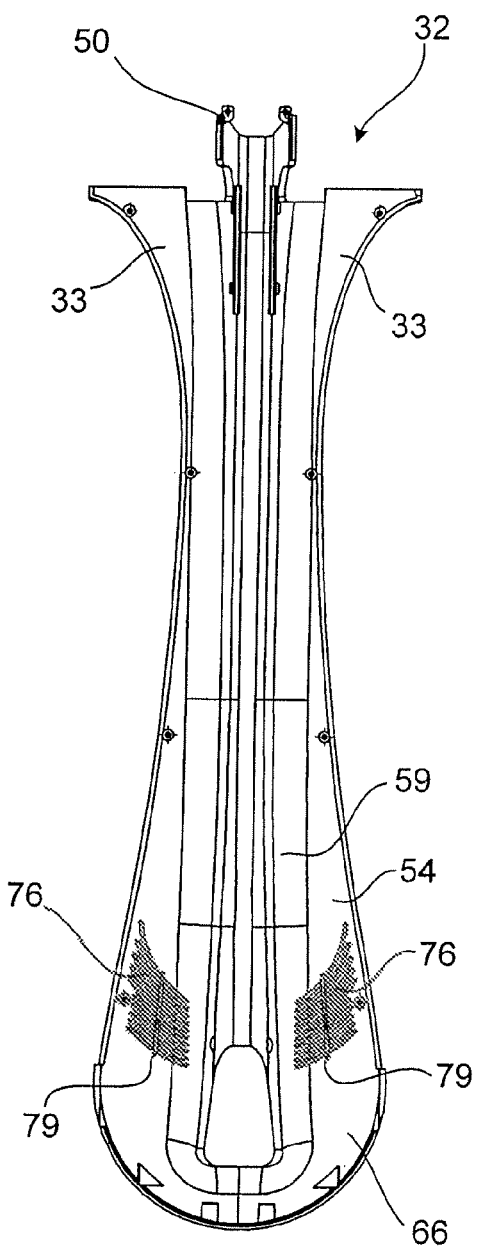
Figure 3C:
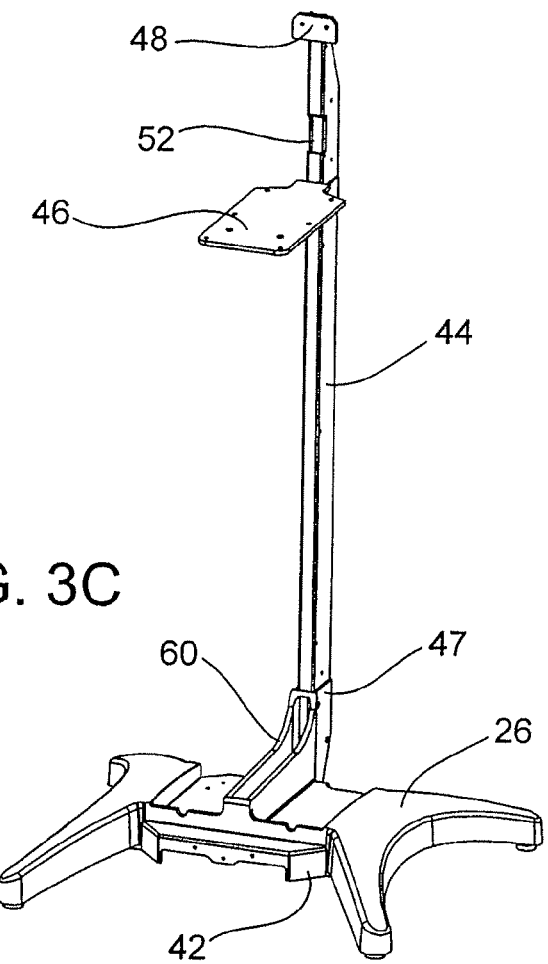
Figure 3D:
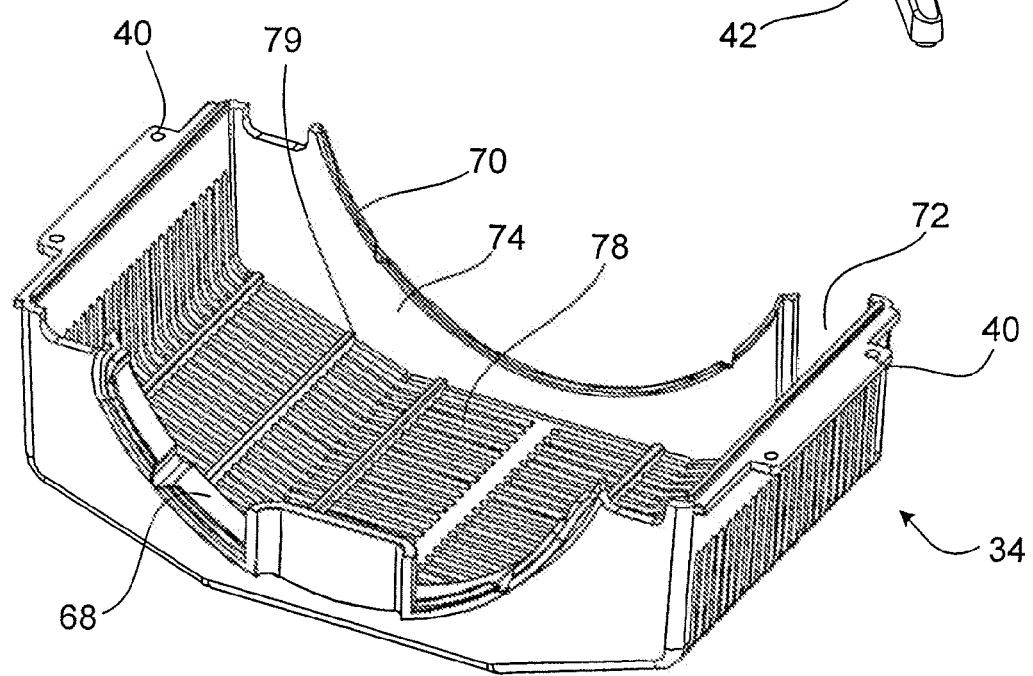
Figure 3E:
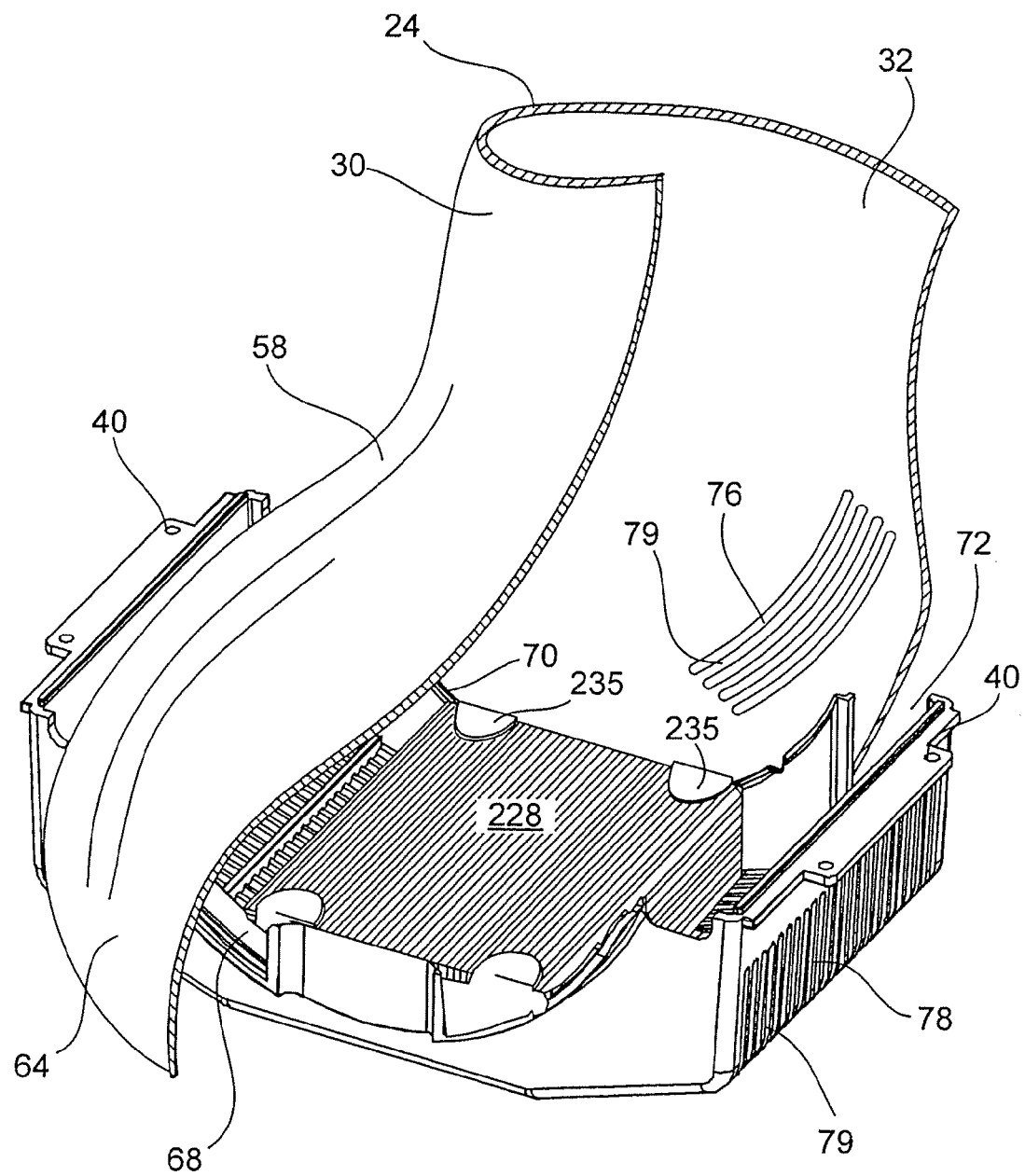
Figure 4:
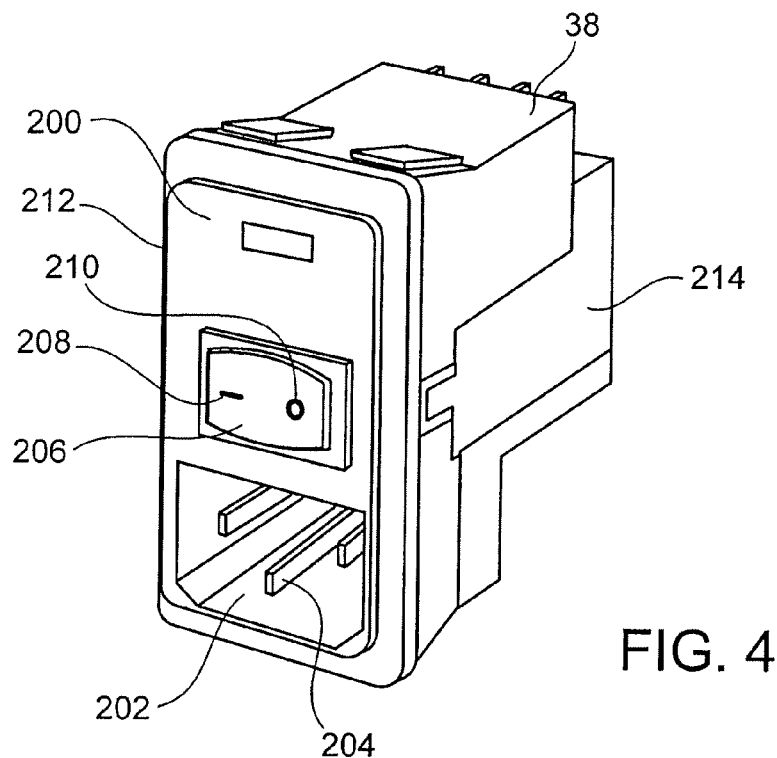
Figure 6:
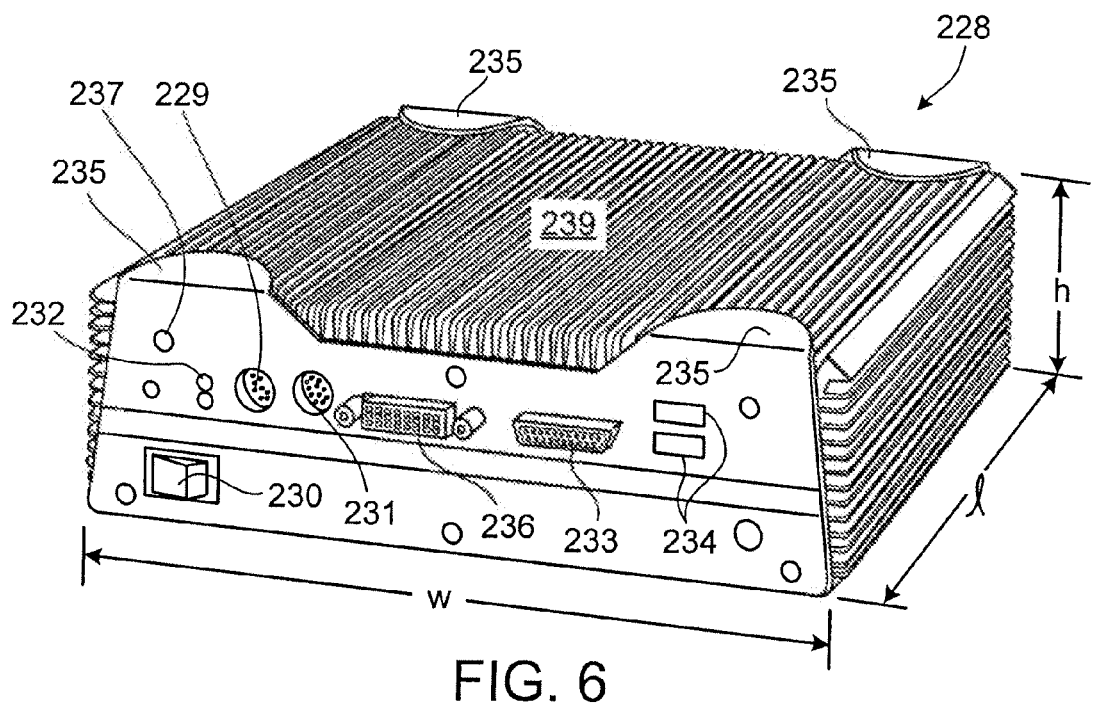
Figure 5:
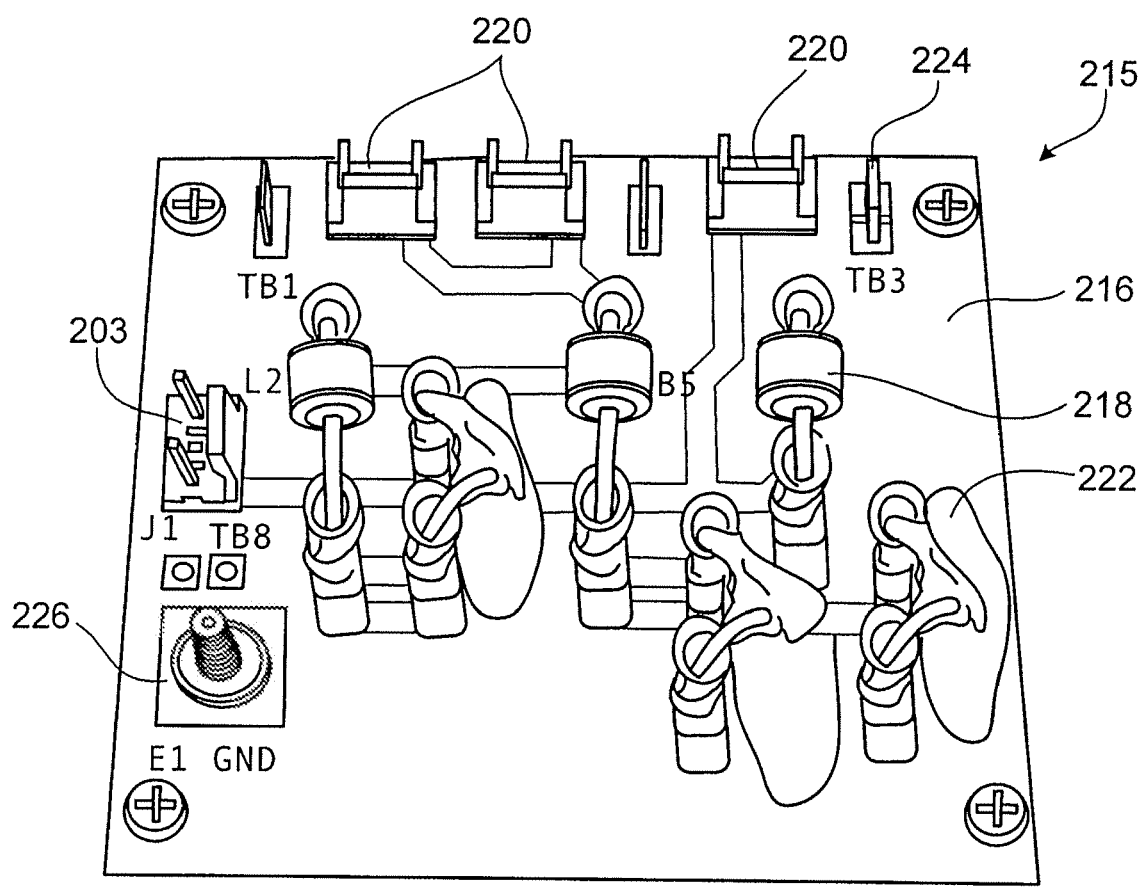

FIG. 1 is a front view of a medical cart.
FIG. 2 is a back view of a medical cart.
FIG. 3 is a side view of a medical cart.
FIGS. 3A, 3B, 3C, 3D, and 7A, 7B, 7C, 7D, 7E, 7F, 7G are perspective views, front views, and top views of components of a medical cart.
FIG. 3E is a schematic perspective view of a part of an assembled medical cart.
FIG. 4 is a perspective view of a power connection module.
FIG. 5 is a perspective view of an AC distribution board.
FIG. 6 is a perspective view of a computer.

Referring to FIGS. 1, 2, and 3, a movable medical device cart 10 is configured to be stable, compact (so that it can be stored in a very small space), and easy and safe to move around within a room or from room to room. A user (such as a doctor or other clinician) can use equipment that is included in the cart in connection with diagnostic or therapeutic procedures, for example, capturing multispectral images of skin lesions and using them to determine whether a biopsy is advisable.

The cart 10 contains and integrates all of the equipment and supplies needed for completing a particular diagnostic or therapeutic procedure, for example, a lesion examination. In some implementations, the user inserts a storage card 29 associated with a particular patient or multiple patients into a card receptacle 18 located on a work surface 20 of the cart 10. The storage card 29 is used to store a variety of patient data. The card receptacle 18 reads and writes data from and to the storage card 29 to and from a computer 228 (FIG. 6) located within a lower portion 22 of a cart backbone 24 (which we also sometimes call a pedestal) adjacent to a cart base 26. The information can be displayed on a touch monitor 28 located above the work surface 20. The touch monitor also provides a user interface to enable a user to interact with application software and to perform a variety of tasks associated with use of the storage card 29.

For example, after the data is processed, the monitor 28 can display to the user that the patient is not qualified to have the lesion examination because, e.g., the storage card 29 has been spent. By spent, we mean, for example, that the available permitted scans, which have been paid for in advance and loaded onto the storage card 29, have been used.

If the data indicates that the patient is qualified for the lesion examination, an imaging device 16 can be activated from its locked state to enable the user to scan the patient's skin. The scanning results obtained by the imaging device 16 can be stored or processed by the computer and displayed to the user for analysis on the monitor 28. In some implementations, the scanning results can be transferred to a different workstation, another computer, or a memory device for storage or analysis using, for example, a memory disk or wireless communication. An example of the storage card 29 that is suitable for use in the medical device cart 10 is discussed in U.S. patent application Ser. No. 12/512,895, filed on the same day as this application, and the entire contents of which are incorporated here by reference.

The medical device cart 10 is designed to be safe, stable, ergonomic, and user friendly. The distance $w_x$ between the front casters 14 and the distance $w_y$ between the front and the casters 12, 14 are chosen to be large enough to make the cart 10 stable, and also small enough to minimize encroachment by the cart into the limited workspace of, for example, a dermatologist's office. In some implementations, the distance $w_x$ between the front casters 14 is about 18 inches to about 20 inches, e.g., 19.09 inches, and the distance $w_y$ between the front caster 14 and the back caster 12 can be about 15 inches to about 18 inches, e.g., 16.06 inches.

The medical cart 10 can be slim and stable. The four casters 12, 14 can be arranged in a square, a rectangle, or other shapes. When projected onto the ground, the largest dimensions of the other portions of the cart 10, e.g., the work surface 20 with a handle 83, the monitor 28, the backbone 24, and the imaging device 16 are substantially the same as or smaller than the dimensions of the square. In some implementations, the 2-dimensional projection of the work surface 20 with the handle 83 has a width that is about 0.5 inch to about 1.0 inch, e.g., about 0.7 inch, larger than the width $w_x$, and another width that is about 0.5 inch to about 1.5 inch, e.g., about 1.1 inch, larger than the width $w_y$. The total height (from the casters 12, 14 to the top of the monitor 28) of the medical cart 10 is 50 about inches to about 55 inches, e.g., 50.1 inches, and is more than two times as large as the widest portion of the cart 10 within a plane perpendicular to the axis of the total height.

The cart 10 can be easily maneuvered and can be stable on a variety of floor surfaces. The casters 12, 14 attached to the case 26 each can flexibly turn in any desired direction. In some implementations, the casters 12, 14 are large and sturdy to overcome uneven floors, e.g., cracks, holes, or even stairs, and can have a diameter of about 3 inches to about 5 inches, e.g., 4 inches.

One or more casters 12, 14 can be locked to resist or stop movement of the cart. In the example shown in FIGS. 1, 2, 3, it is the front casters 14 that are lockable. The base 26 can be cast of a relatively heavy material, for example, cast steel, to help to lower the center of gravity 11 of the cart 10 and to provide structural rigidity and stability. By an effective arrangement of the components of the cart, the center of gravity 11 of the cart 10 is located at point which is about ¼ to about ½, e.g., ⅓, of the total height of the cart 10 from the floor. For example, the center of gravity 11 of the cart 10 is about 15 inches to about 20 inches from the floor, e.g., about 18.5 inches to about 19 inches from the floor. A vertical line that passes through the point of the center of gravity 11 of the entire cart 10 passes through a point, e.g., the symmetry center 13, within the square, rectangle, or other shape formed by the four casters 12, 14 in a plane, e.g., perpendicular to the height of the cart 10. By keeping the center of gravity 11 low, the stability of the cart 10 is enhanced. The cart 10 can move or be locked on a slope of about 10 degrees to about 15 degrees without tipping.

The backbone 24 rises vertically from and connects at its bottom end 22 to the base 26. The backbone 24 at its top end 33 is connected to a bottom of the work surface 20. The backbone 24 has a shell 36 enclosing a hollow interior (formed by a space 59 shown in FIG. 3B) to provide room for wires, e.g., power lines and cables (not shown), connecting a power connection module 38, the computer located at or in the bottom 22 of the backbone 24, the monitor 28, the card receptacle 18, and/or the imaging scanner 16 (which we also sometimes call a probe) to provide power and other connections, e.g., USB connections, to devices located near the work surface 20. For example, the computer, the monitor 28, the card receptacle 18, and the imaging device 16 can be powered when the power connection module 38 is connected to a power main and has its power switch (FIG. 4) turned on, and the computer can communicate with the monitor 28, the card receptacle 18, and the imaging device 16 using, for example, Ethernet cables (not shown).

The backbone shell 36 has smooth, curved side walls 37 that taper in from the bottom 22 of the backbone 24 towards the work surface 20. This pyramid-shaped design also enhances the stability of the cart 10. The shape of the backbone shell provides clearance for the knees and/or legs of the user when seated in a chair and working at the cart 10.

Referring to FIGS. 3A-3D, the shell 36 of the backbone 24 (FIG. 1) also houses a vertical support pole 44 that is welded at a bottom end 47 to the base 26 and connects the monitor 28, the work surface 20, and the base 26 (perspective view). The welded support pole 44 provides the cart 10 with mechanical strength and resistance to torsion, among other things. In particular, the support pole 44 has one end 47 welded or screwed to the base 26 and covered by the backbone 24, another end 48 extending from the backbone 24 and including mechanisms, such as screws holes, for fastening the monitor 28 onto the cart 10. Between the two ends 47, 48, the support pole 44 also includes a flat piece 46 extending horizontally towards the front of the cart 10 to fasten the work surface 20 and the backbone 24.

The shell 36 can be assembled using a front piece 30 (perspective view), a back piece 32 (front view), and a bottom piece 34 (perspective view) and can be mounted onto the base 26 using the welded support pole 44. The front piece 30 is arranged vertically adjacent to the support pole 48. When assembled, a curved bottom 58 of the front piece rests on the curved upper surface 60 of the base 26 and the flat piece 46 attached to the support pole 44 extends from the interior of the backbone 24 out from a recessed dent 56 of the front piece 30. The back piece 32 has a curved surface 54 that defines an interior space 59 so that when the front and back pieces 30, 32 are assembled, e.g., screwed together, a hollow interior is formed. The back piece 32 also includes a clamp 50 that, when assembled, clamps the support pole 44 to further stabilize the whole cart 10. The bottom piece 40 is assembled under the bottom 42 of the base 26 using, e.g., screw holes 40. The bottom curved surfaces 64, 66 of the front and back pieces 32, 34 match with the front and back curved surfaces 68, 70 of the bottom piece 34, respectively, to make the cart 100 better looking. The power connection module 38 can be installed at an opening 72 at the back surface 74 of the bottom piece 34.

Referring to FIG. 3E, the computer 228 can be mounted within the bottom piece 34 under the base 26 (not shown) and covered by the backbone 24. The low position of the computer lowers the center of gravity of the cart and provides stability. The back piece 32 and the bottom piece 34 include a pattern of long, thin vents 67, 78 (FIG. 3D), e.g., in the form of openings between grid elements 79, to provide ventilation and dissipate heat generated by the power connection module 28 and the computer 228 (see also, FIGS. 3B and 3D). In addition, the steel material used in the base 26 also effectively conducts heat from the backbone 24 to reduce the temperature around the computer area and provides a good electrical ground for the electrical devices mounted on the cart 10.

The backbone 24 and the support pole 44 can be made, for example, of a molded or cast polymer, e.g., a polyurethane elastomer. The polymer material can be light and can reduce the total weight of the cart 10. The total weight of the cart 10 is about 60 pounds to about 100 pounds, e.g., about 70 pounds. In addition, the backbone 24 has a larger dimension and uses more material at its lower portion than its higher portion. The center of gravity is kept low to provide stability to the cart 10.

FIG. 4 shows the power connection module 38 that is installed in the opening 72 of the bottom piece 34 of the back bone 24. The user can access the power connection module 38 through a front face 200 facing the user when the module 38 is assembled onto the backbone 24. For example, a power main can be connected to the module 38 through an input connector 202 containing prongs 204 or other suitable connectors. In some implementation, a power cord (not shown) suitable for connecting the power connection module 38 to the power main is provided with the cart 10. A voltage, e.g., a line voltage, can be supplied to an AC distribution board (FIG. 5) located behind the front surface 200 and fuses 212, which are used for protecting the AC distribution board and the devices from power overloading. When a power switch 206 is switched on 208 or off 210, the AC distribution board supplies or cuts power to the imaging device 16, the computer in the bottom of the backbone 24, and the monitor 28, through wires held within the backbone 24. In a back portion 214 of the module 38, which includes a fuse, an electrical noise filter (not shown) can be installed to filter out noise to meet a medical standard in the power supplied to each device. In some implementations, the electrical noise filter can be a commercially-available, medical grade noise filter.

An example of an AC distribution board 215 is shown in FIG. 5. Wires (not shown), e.g., power cords, can be used to connect one or more, e.g., at least three, output connectors 220 located on a board 216 and power receiving devices, such as the monitor 28 (FIG. 1), to distribute the power supplied from the input connector 202 and received by the input port 203 to the power receiving devices. The AC distribution board 215 also includes gas discharge tubes 218 and thermally-protected metal oxide varistors 222 to suppress electrical surge in the input/output connectors 202, 220 and one or more electrical ground connections 224, 226.

An example of a computer 228 to be placed in the bottom portion 22 of the backbone 24 and used with the cart 10 is shown in FIG. 6. The computer 228 contains input and output ports, e.g., a power port, one or more Ethernet ports, keyboard or mouse port, and others (not shown, which are on a surface of the computer not visible in FIG. 6), for communicating with peripherals, such as the imaging device 16, a keyboard connected to the computer, the card receptacle 18, and the monitor 28. The computer 228 is compact and the operation of the computer can be quiet because no fan is used in the computer. For example, the computer 228 has a height h of about 640 mm to about 650 mm, e.g., about 642.8 mm, a length l of about 150 mm to about 160 mm, e.g., 156 mm, and a width w of about 210 mm to about 220 mm, e.g., 212 mm. Other dimensions can also be used. The computer 228 can have the following features, for example: an Intel Core Duo L7400 processor operating at a frequency of about 1.5 GHz and with an internal Double Data Rate (DDR) II, a Small Outline Dual In-Line Memory Module (SODIMM) with a 2 gigabyte (GB) memory, a power ON/OFF switch 230, a power LED indicator 232, a reset switch, one or more, e.g., four, Universal Serial Bus (USB) ports 234 (not all shown), a digital video interface (DVI) connection 236, and others, e.g., one or more flash drives. In addition, the computer 228 also includes other features, such as other ports, e.g., an audio port 229, a S-video port 231, and a LVDS port 233, and a hard disk drive LED 237. Computers having other sizes or features can also be used. Pads 235 are attached to the surface 239 of the computer 228, for example, to help support the computer 228.

Software can be installed on the computer 228 for use in connection with the scanning, imaging, data processing, and other operations. For example, a Windows® XP operating system can be loaded onto the computer 228. In addition, USB drivers can be used to enable other software, for example, MelaFind application software, installed on the computer 228 to communicate with the imaging device 16 using a USB communications protocol. In some implementations, the imaging device 16 can also communicate with the computer 228 through a wireless protocol. The MelaFind application software can allow the user to use the imaging device 16 for the purposes of point-of-care imaging and image analysis. The use of the software, e.g., the MelaFind application software, is also discussed in U.S. patent application Ser. No. 11/761,816, filed on Jun. 12, 2007, the entire contents of which are incorporated here by reference.

Referring again to FIGS. 1, 2, and 3, a work table 19 including the work surface 20 is located at a countertop height, e.g., about 2 feet to about 4 feet or about 3 feet above the ground, so that the user can stand or be comfortably seated when operating the workstation 19 or in preparation for or following a diagnostic or therapeutic procedure. A handle 83, which includes a left handle 84 and a right handle 82, wraps around the work table 19 to enable the user to hold and move the cart 10. The imaging device 16 is held on a cradle 86 to the right of the work surface 20 by a hanger 88 above the work surface 20 to prevent the imaging device 16 from falling off the work table 19, for example, during the movement of the cart 10. In addition, a head 104 of the imaging device 16 is protected by a over-hanging piece 21 extending under the work surface 20 and the head 104 (see also, FIG. 7G). A cable 158, e.g., a power cable or a USB cable, including a coiled portion 160 is connected to a USB port located at the bottom of the work table 19 near the imaging device 16. The USB port is connected to the computer 228 at the lower portion 22 of the backbone 24 using, e.g., a single cord, and the connected cable 158 can provide both power and computer connection to the imaging device 16. When the coils of 160 are stretched, the cable 158 can provide a total of about 4 feet to about 8 feet, e.g., 5 feet, work length. During operation, the user can move the imaging device 16 flexibly and extensively without moving the cart 10 or over-stretching the cable 158. In some implementations, more USB ports are placed on the backbone 24 to enable the user to use other devices, such as a memory stick to, for example, transfer data.

In some implementations, one or more, e.g., two, bottles 94 of alcohol or other liquid for medical use can be placed on the work surface 20 in one or more wells 96 each having a diameter corresponding to a standard diameter of the bottles 94, e.g., about 1.4 inches to about 1.5 inches or 1.42 inches, in diameter. For example, before the scanning, the user can use the alcohol to clean the patient's skin. Alcohol (or other suitable liquid) can also be applied as an optical coupling medium between the skin and the imaging device. The wells 96 (see also, FIG. 4) can be defined in the surface 20 or can be made of walls extending from the surface 20 (not shown). The wells 96 can have a suitable depth to prevent movement or falling of the bottles 94 on work surface 20. Other suitable methods or forms of securing mechanisms can be used for safe placement of the bottles.

Under the work surface 20, two trays 90, 92 arranged on top of each other are attached to the work table 19. The top tray 90 contains a computer keyboard (not shown) connected to the computer 228 and/or the touch monitor 28. When the top tray 90 is drawn out, the user can use the keyboard to enter data, such as patient data, into the computer. The keyboard is easily accessible and can be protected by the closed drawer from, e.g., liquid spills or other contaminants. Because the keyboard is not placed on the work surface 20, the space on the work surface 20 is available for other uses, for example, placing papers, cards, and other medical supplies for the procedure being performed. The keyboard can include all functional keys that a commercial keyboard has and can be small to fit into the tray 90. The bottom tray 92 can be an auxiliary drawer that allows the user to store operational supplies and provide other convenience storage to the user.

Other than the USB port for the imaging device 16 for power and signal connections, a USB hub that includes one or more, e.g., two or three, or even more, USB ports, is mounted on the bottom of the work table 19, e.g., the bottom of the top tray 90. Each USB cable is connected to the power supplied from the power connection module 38 and the computer 228, through wires housed in the backbone 24. In some implementations, the keyboard on the top tray 90 can be connected to one USB port for power and computer connection. Additional USB ports can be used for other external devices, e.g., memory sticks, for transferring and storing data, system checking, and other procedures and uses.

Referring to FIGS. 7A-7G, the work table 19 can be partially assembled using a cast table 98 (perspective view), the right handle 82 (perspective view), the left handle 84 (top view), the hanger 88 (perspective view), the over-hanging piece 21 (perspective view) and the card receptacle 18 (perspective view). The cast table 98 is made to have a maximum surface area to provide a large work space while being small enough to maintain the stability of the cart 10. In some implementations, the dimensions of the cast table 98 projected in the plane of the work surface 20 is the same as or less than the area covered by the casters 12, 14 of the cart. The cast table 98 is made of a polymer, e.g., a polyurethane elastomer, to be light weight. To further reduce the weight, the cast table 98 can be made of a plastic layer 152 thinner than the total thickness l of the table and reinforced by ridges 154 shown in the bottom perspective view 156 of the table 98. The ridges 154 can be in the form of grids or any other desired forms.

The cradle 86 for positioning the imaging device 16 includes an opening 100 defined in a surface 102 that has a tilt angle $\alpha$, e.g., of about 30° to about 45° relative to the work surface 20. The opening 100 can have a diameter, e.g., of about 3.5 inches to about 4.0 inches, suitable for receiving the imaging head 104 of the imaging device 16 (FIG. 1). The surface 102 tilts from a high end 108 near the back of the cart 10 towards a lower end 110 in the front of the cart 10 and can facilitate accessing from the front of the cart 10 to place or remove the imaging device 16 onto or from the cart 10. Such an arrangement can also provide visual appeal to the cart 10.

The hanger 88 can also be made of a cast polymer and can be attached to the lower end 110 of the cradle 86 using, for example, alignment and fastening mechanisms 112 at the bottom of the hanger 88 and matching mechanisms 114 on the cradle 86. When assembled, two arms 116, 118 of the hanger 88 extend beyond the surface 102, e.g., form an angle of about 60 degrees to about 100 degrees with the surface 102, to hold an imaging device holder 106 of the imaging device 16 in an opening 120 between the arms 116, 118.

Figure 7A:
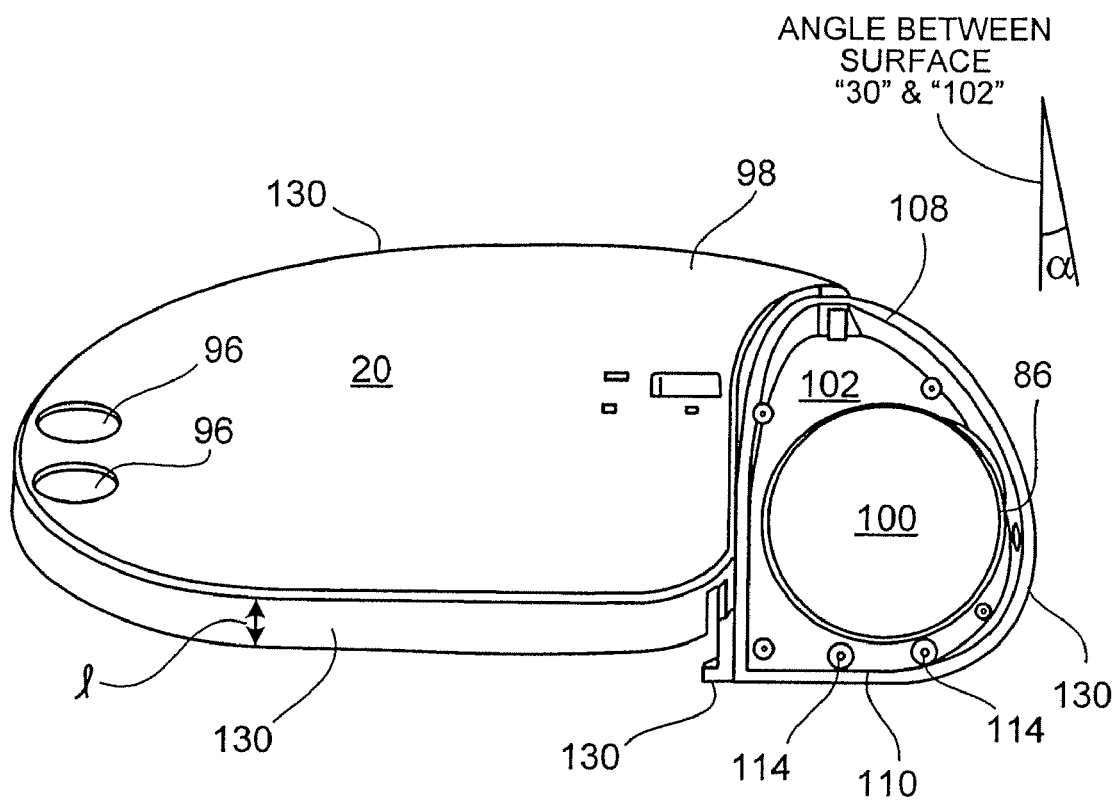
Figure 7B:
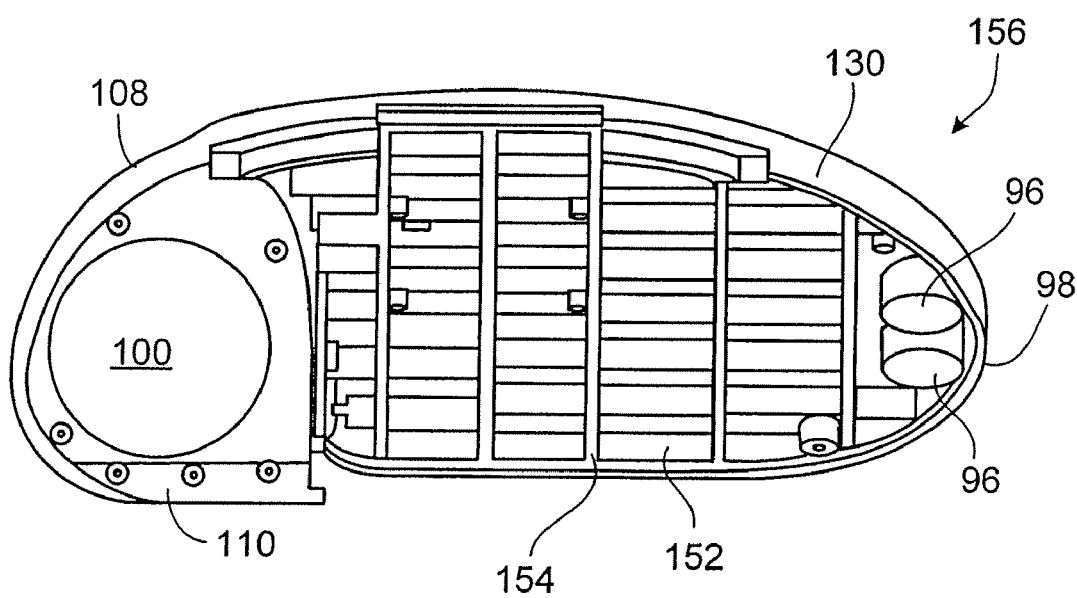
Figure 7C:
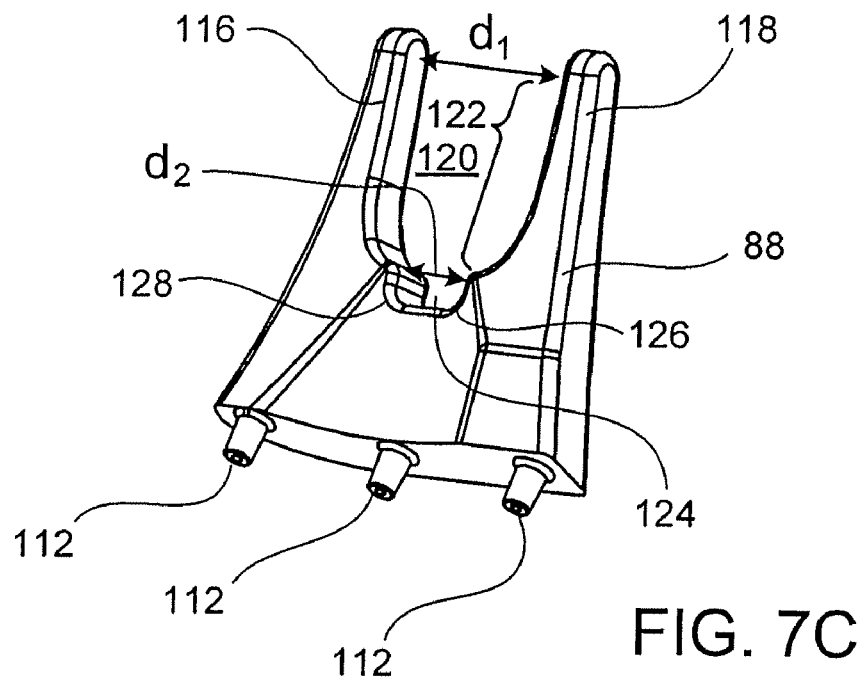
Figure 7D:
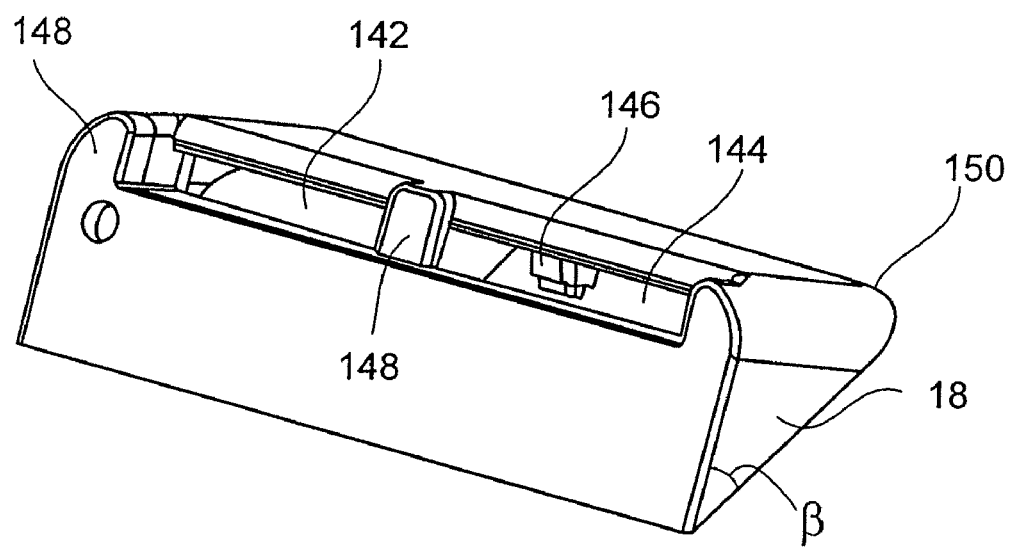
Figure 7E:
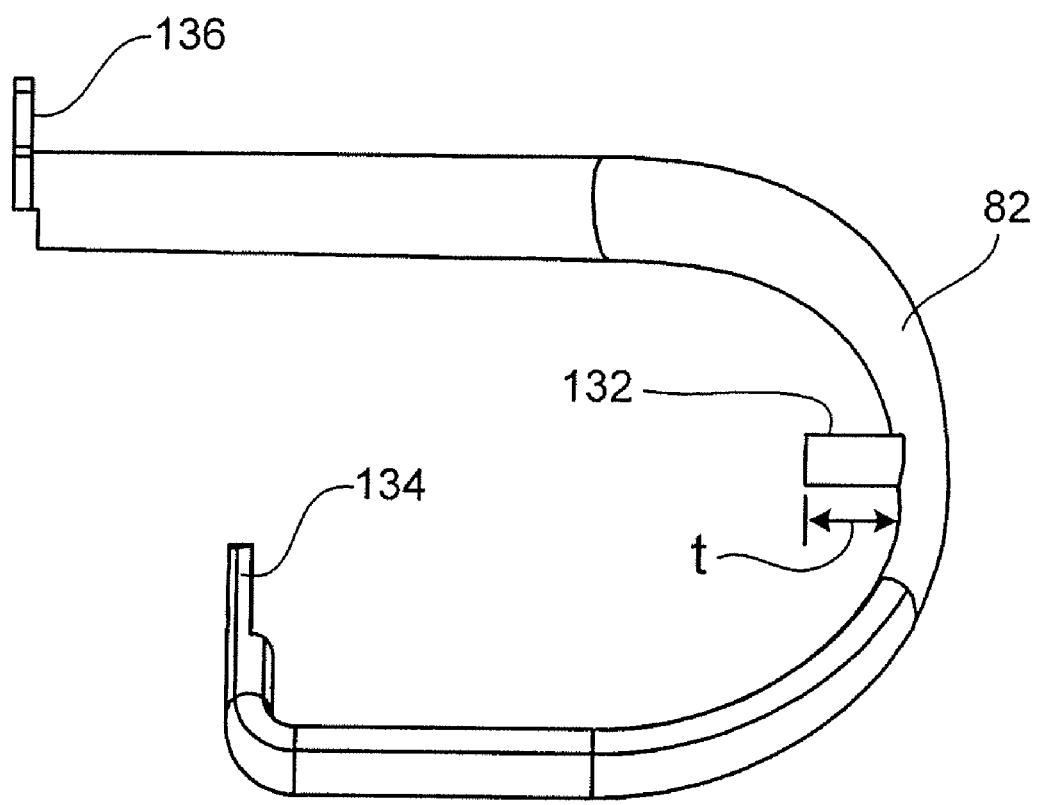
Figure 7F:
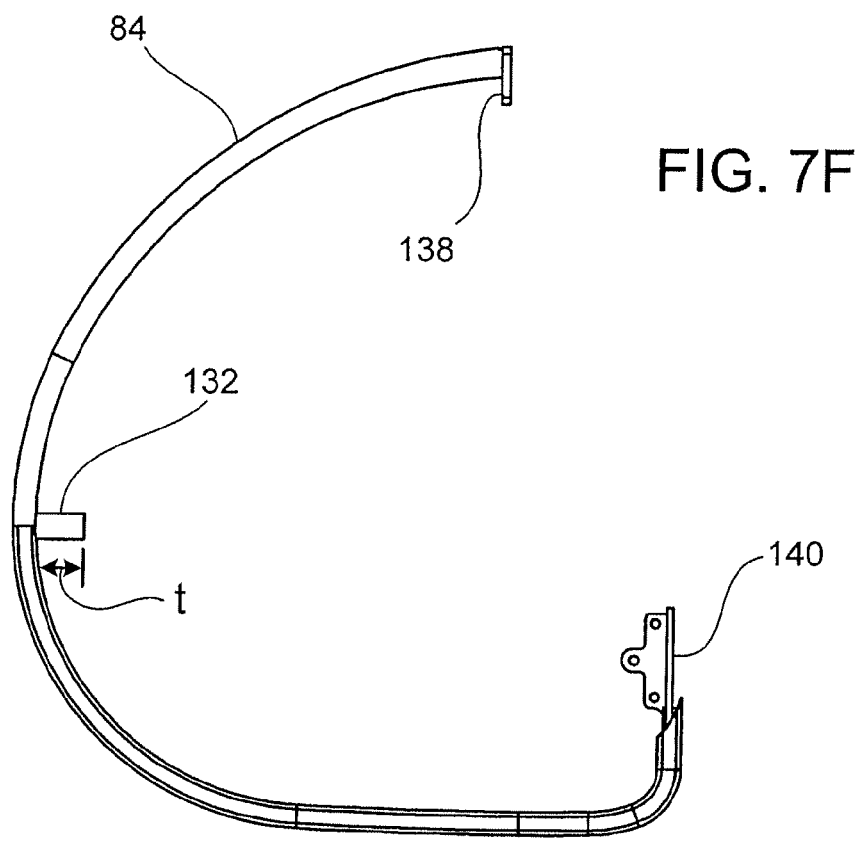
Figure 7G:
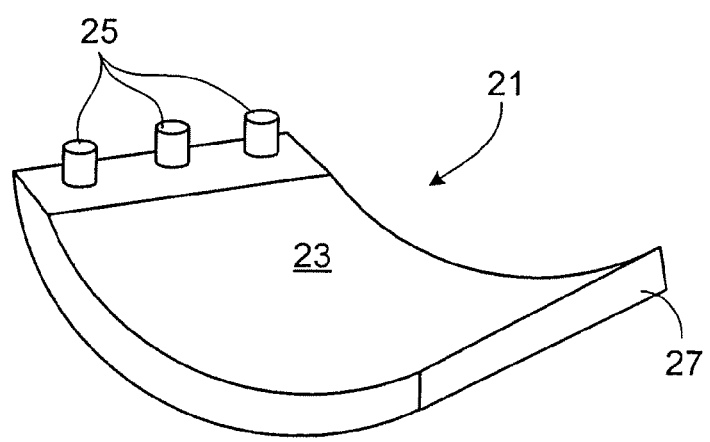

The over-hanging piece 21 has a curved surface 23 that follows the curvature of the head 104 of the imaging device (FIG. 1) and can be attached to the cast table 98 of FIG. 7A at an opposite surface of the surface that includes matching mechanisms 114. The over-hanging piece 21 extends from the front of the cart 10 towards the back of the cart 10 and protects the imaging device resting on the cart. A far end 27 of the over-hanging piece 21 can be selected to extend to a distance as desired.

The opening 120 includes an outer portion 122 having a diameter $d_1$ and an inner portion 124 having a diameter $d_2$ smaller than $d_1$. The small diameter $d_2$ is, e.g., about 0.7 inch, and is substantially the same as or slightly less than a diameter of the imaging device holder 106, so that when the imaging device holder 106 is pressed into the inner portion 124 of the opening 120, the hanger 88 tightly holds the imaging device 16. The large diameter $d_1$ is, e.g., about 1.6 inches to about 1.8 inches, so that the imaging device holder 106 can be easily placed between the arms 116, 118. The diameter $d_1$ is kept smaller than a diameter of the imaging head 104 so that the arms 116, 118 can support the imaging head 104. The arms 116, 118 and the attachment between the mechanisms 112, 114 are built to be strong to prevent the imaging device 16 from moving or falling during the movement of the cart 10. In some implementations, two walls 126, 128 defining the diameter $d_2$ of the inner portion 124 can be surfaces of flexures (not shown). The diameter $d_2$ can be smaller than the diameter of the imaging device holder 106. In use, the imaging device holder 106 pushes against the flexures to fit into the inner portion 124 and can be tightly held by the forces exerted by the deformed flexures.

The right and left handles 82, 84 wrap around the circumference 130 of the cast table 98 and have an average distance t, e.g., about 1 inch to about 2 inches, from the circumference 130 for the user's hand(s) to hold the handles and move the cart 10. The shape of the handles 82, 84 can be ergonomic. The handles 82, 84 are made of a metallic core, e.g., stainless steel or other suitable metal, that has been formed to the proper shape, and coated with a molded plastic to provide sufficient strength to the handles while keeping the total weight low. Each handle 82, 84 can include a sleeve 132 made, e.g., of a metal, that connects to the cast table 98 and maintains the distance t between the circumference 130 and the handles 82, 84. The handles 82, 84 are secured to the table 98 using the securing mechanisms 134, 136, 138, 140. The securing mechanisms 136-140 can include hinges, screws, alignment datums, and other suitable forms.

The card receptacle 18 can include two openings 142, 144 separated by an alignment tab 148 to receive the storage card 29. A reading device 146 is located with the openings 142, 144 to read the data/information from the inserted exam card. The openings 142, 144 extend from an elevated end 148 toward another low end 150 that meets the bottom of the card receptacle 18, forming an angle $\beta$, e.g., of about 20 degrees to about 40 degrees or 30 degrees, with the bottom of the card receptacle 18, and therefore, the work surface 20 when assembled. The tilted openings 142, 144 can make the insertion of the storage card 29 easy. The card receptacle 18 and the storage card 29 are also described in the U.S. patent application Ser. No. 12/512,895, filed on the same day as this application and incorporated here by reference.

Referring again to FIGS. 1, 2, and 3, the monitor 28 provides an interface between the user and the software or programs stored on the computer 228 for processing the data obtained from the operation using the imaging device 16. The monitor 28 can be a commercially available, 19-inch, wide, flat screen monitor so that the displayed contents are large enough to be viewed from a distance to make it easy to use the software and hardware in connection with the procedure. For example, the user does not have to walk back and forth between the patient and the monitor 28 to scan the patient and view the data/information collected or displayed by the monitor 28. The monitor 28 is sensitive to a light finger pressure. The user can select menu options by lightly touching the monitor 28 on displayed menu choices. The monitor 28 is raised above the work surface 20 by the neck 62 to provide a comfortable view to the user that is about five feet tall to about 6 feet tall. The neck 62 can include a shell covering the portion of the support pole 44 that extends beyond the backbone shell 36 to provide a uniform color and structure. The monitor 28 is connected to a hinge (not shown) and can be swiveled up or down, based on the user's viewing preference. A power indicator 178, e.g., a LED light, can indicate that power is being supplied to the monitor 28. The user can also reset the computer and/or the monitor 28 by pressing on a reset bottom 176 exposed on the neck 62.

The monitor 28 is set in a bezel 164 of a casing 162 defined by surrounding walls 166. The back 168 of the casing 162 includes openings 170 in the form, e.g., of a grid, to serve as air vents for the monitor 28 and dissipate heat generated by running the monitor 28. In addition, a cover 172 is used to cover an opening in the back 168 that allows the hinge connected to the monitor 28 to extend from the basing 162 so that the back 168 of the monitor 28 has a uniform cover to be visually appealing. The casing 162 is slim and has dimensions based on the dimensions of the monitor 28. The monitor 28 can be assembled in the casing without using screws, e.g., the casing 162 can be snapped together about the monitor 28. The casing 162 also includes a power cord hook 174 to hang the power cord (not shown) connected to the power connection module 38 and to prevent the cart 10 or the user from running over the power cord.

Other implementations and applications are also within the scope of the claims.

For example, the imaging device 18 used for lesion scanning can be a MelaFind® scanner of the kind developed by Electro-Optical Sciences of Irvington, N.Y., and aspects of which are described for example, in U.S. Pat. No. 6,081,612, filed Feb. 27, 1998, U.S. Pat. No. 6,208,749, filed Feb. 27, 1998, U.S. Pat. No. 6,307,957, filed Jun. 27, 2000, U.S. Pat. No. 6,563,616, filed Feb. 21, 1999, U.S. Pat. No. 6,626,558, filed Aug. 31, 2001, U.S. Pat. No. 6,657,798, filed Feb. 10, 2003, U.S. Pat. No. 6,710,947, filed Feb. 10, 2003, U.S. Pat. No. 7,102,672, filed Feb. 8, 2002, and U.S. Pat. No. 7,127,094, filed Jan. 2, 2003, and U.S. patent application Ser. No. 11/500,197, filed Aug. 7, 2006, Ser. No. 11/681,345, filed Mar. 2, 2007, Ser. No. 11/761,816, filed Jun. 12, 2007, and Ser. No. 11/956,918, filed Dec. 14, 2007, each incorporated here by reference. Among other advantages, the MelaFind scanner makes contact with the lesion during scanning, shielding it from ambient light, and provides carefully controlled lighting of the lesion in multiple spectral bands to produce images, making the image information acquired during the scans repeatable and consistent. Other digital scanners can also be used. Examples are provided in U.S. patent application Ser. No. 12/204,247, filed Sep. 4, 2008, which is incorporated here by reference.

The cart 10 can be in colors having white and off-white tones. Other colors can be chosen.

The backbone 24 and/or the neck 62 can have an adjustable height to allow people of different heights or in different positions, e.g., sitting or standing, to operate the cart 10 comfortably.

One or more fans can be included in the computer 228, the backbone 24, or the casing 162 to help heat dissipation and reduce the working temperature of the computer 228 and/or the monitor 28. Other software, such as Word or Excel, can be installed on the computer 228. In addition to the keyboard on the keyboard tray 90, a mouse can be provided to facilitate the use of the computer.

The computer 228 can be capable of wireless communication with a network, e.g., Internet. The computer 228 can include a port for network connection. The network connection port can be exposed to the user at various locations of the cart 10, e.g., the backbone 24, the neck 62, the work surface 20, or the power connection module 38. Data, e.g., imaging data or processed imaging data can be transferred to a desired location for storage or further analysis using these communication protocols.

The card receptacle 18 and/or the cradle 86 and the hanger 88 can be placed at different locations from what is shown in the figures. More drawers can be included in the workstation 19. The work surface 20 can be smooth or separated into patterns or grids. The backbone 24 can be in shapes other than what is shown in the figures.

More than one card receptacles 18 can be placed on the work surface 20. In some implementations, two storage cards that contain diagnosis data taken at different times can be read simultaneously by the card receptacles and displayed on the monitor 28, e.g., for comparison.

Other polymers suitable for use in medical devices can be used for the various components of the cart 10.

A wide variety of different kinds of equipment for different medical purposes can be included on the cart.

What is claimed is:

1. An apparatus comprising
a movable medical device cart that has a work surface that has a front end and a back end a cart base that has a front end and a back end, legs mounted on the cart base, casters mounted on the legs, and a single pedestal that has a hollow lower end connected at the back end of the cart base and an upper end connected at the back end of the work surface,
a probe for electronically imaging skin of a patient and accessible at the work surface,
a computer mounted on the cart base and within the hollow lower end of the pedestal to sink heat away from the computer,
a handle that extends along at least a portion of the front end of the work surface and along at least half of a perimeter of the work surface, and
a center of gravity that is no higher than about ⅓ of a total height of the apparatus from a floor on which the apparatus stands,
the apparatus being stable on a surface having a tilt angle up to about 15 degrees.

2. The apparatus of claim 1 in which the legs comprise a metal.

3. The apparatus of claim 1 also comprising connections extending within the pedestal from the computer to the probe.

4. The apparatus of claim 1 comprising an electronic device that comprises a display.

5. The apparatus of claim 1 comprising an electronic device that comprises a receptacle for a memory card.

6. The apparatus of claim 1 in which the work surface is at a height for a seated or standing adult to work, and the breadth of the work surface is less than one-half of a height of the pedestal.

7. The apparatus of claim 1 in which the work surface is at a height for an adult to work, and the breadth of the legs is less than one-half of the height of the work surface.

8. The apparatus of claim 1 in which there are four legs.

9. The apparatus of claim 1 in which two of the legs span a width of about 18 inches to about 20 inches along a first direction.

10. The apparatus of claim 9 in which two of the legs span a width of about 15 inches to about 18 inches along a second direction different from the first direction.

11. The apparatus of claim 1 in which the handle is in an ergonomic shape.

12. The apparatus of claim 1 in which the handle includes a metal core and a plastic shell.

13. The apparatus of claim 1 in which the pedestal is hollow and houses wires connecting a power supply to one or more of the electronic devices.

14. The apparatus of claim 1 also including one or more USB ports adjacent to the work surface.

15. The apparatus of claim 1 comprising an electronic device that comprises a touch monitor.

16. The apparatus of claim 15 in which the monitor is set in a bezel of a casing.

17. The apparatus of claim 16 in which the casing is assembled about the monitor by snapping.

18. The apparatus of claim 1 in which the handle is spaced from the work surface by a gap that is large enough to receive a hand of a user that is holding the handle.

19. The apparatus of claim 18 in which the handle is attached to the work surface by spars at attachment locations along a length of the handle.

20. The apparatus of claim 19 in which the handle has a cross-section that enables a user's hand to grasp the handle at locations along its length.

* * * * *